Figure 1:
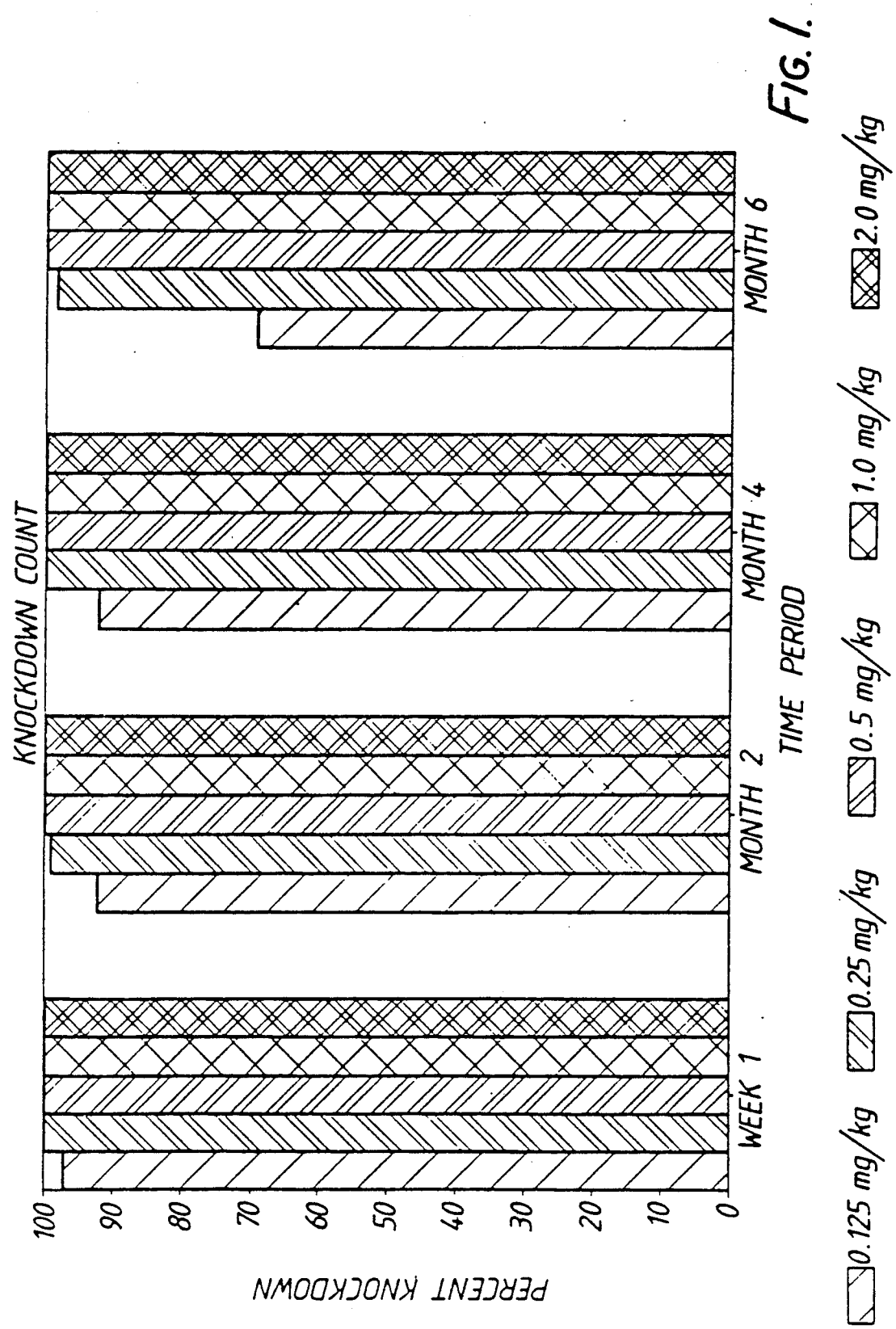

United States Patent [19]

Dawson

[11] Patent Number: 5,037,653
[45] Date of Patent: Aug. 6, 1991

[54] PESTICIDAL CHEMICAL FORMULATIONS

[75] Inventor: Howard B. Dawson, Allestree, Great Britain

[73] Assignee: NC Development Inc., Irving, Tex.

[21] Appl. No.: 435,441

[22] PCT Filed: Mar. 30, 1988

[86] PCT No.: PCT/GB88/00239
§ 371 Date: Nov. 20, 1988
§ 102(e) Date: Nov. 20, 1988

[87] PCT Pub. No.: WO88/07326
PCT Pub. Date: Oct. 6, 1988

[30] Foreign Application Priority Data

Mar. 30, 1987 [GB] United Kingdom ............... 8707563
Jan. 26, 1988 [GB] United Kingdom ............... 8801643

[51] Int. Cl.$^5$ .................................... A01N 25/00
[52] U.S. Cl. ................................. 424/405; 514/531; 514/521
[58] Field of Search .................. 514/531, 521; 424/405

[56] References Cited

U.S. PATENT DOCUMENTS

| | | | |
|---|---|---|---|
| 3,954,967 | 5/1976 | Urton | 424/81 |
| 4,500,348 | 2/1985 | Hausmann et al. | 71/103 |
| 4,567,161 | 1/1986 | Posanski et al. | 514/23 |
| 4,737,520 | 4/1988 | Naik et al. | 514/520 |

FOREIGN PATENT DOCUMENTS

| | | |
|---|---|---|
| 1007985 | 1/1974 | Canada . |
| 1209361 | 5/1984 | Canada . |
| 0302701 | 2/1989 | European Pat. Off. . |
| 2326077 | 1/1974 | Fed. Rep. of Germany . |
| 2335347 | 2/1974 | Fed. Rep. of Germany . |
| 2439177 | 2/1975 | Fed. Rep. of Germany . |
| 2437882 | 4/1975 | Fed. Rep. of Germany . |
| 2544150 | 4/1976 | Fed. Rep. of Germany . |
| 1026169 | 4/1953 | France . |

Primary Examiner—Thurman Page
Assistant Examiner—D. Gabrielle Phelan
Attorney, Agent, or Firm—Foley & Lardner

[57] ABSTRACT

Water-miscible pesticidal formulations whose average particle size is at most 200 nm include water, oil, a surfactant, and a cosurfactant, wherein either the oil is a pesticide or the formulation comprises a pesticide dissolved in the oil. The pesticide may be a pyrethroid such as cypermethrin or deltamethrin. The formulations can be molecular solutions, micellar solutions or microemulsions (water-in-oil or oil-in-water) and are generally clear. They exhibit improved activity over conventional pesticidal formulations, particularly in the protection of grain, fruit and brassica plants and against insects, mites and/or larvae. The formulations are especially useful in protecting stored grain, for example against the lesser grain borer weevil (*Rhyzopertha dominica*).

19 Claims, 3 Drawing Sheets

PESTICIDAL CHEMICAL FORMULATIONS

This invention relates to chemical formulations which are useful as water-miscible preparations of compounds which are normally regarded as water-insoluble and to their use as pesticidal formulation.

Some of the most useful compounds in industry and agriculture are not water soluble This often inhibits or curtails their use, particularly when the application of the compound in solution is desirable. Although the compound may well be soluble in organic solvents, their use in large quantities is not always desirable from the economic or environmental point of view.

One such group of compounds comprises pesticides, for example the pyrethroid pesticides, which are widely used commercially either as:

a. 5 g/l–500 g/l agrochemical concentrates for use after dilution with water; or as
b. 0.1 g/l–1.0 g/l ready-for-use (rfu) formulations for public health areas.

Typical solvents used in these systems include hydrocarbons such as xylene, heavy aromatic naphtha, kerosene and various paraffins or alkanes.

One synthetic pyrethroid is deltamethrin, which is the common name for 3-(2,2-dibromoethenyl)-2,2-dimethylcyclopropane carboxylic acid cyano(3-phenoxyphenyl)methyl ester. Deltamethrin is a potent synthetic pyrethroid pesticide, the preparation of the racemic mixture of which is described in DE-A-2439177. Deltamethrin is insoluble in water, but is soluble in organic solvents such as ethanol, acetone, dioxane, xylene and certain petroleum fractions Other synthetic pyrethroids include cypermethrin (3-(2,2-dichloroethenyl)-2,2-dimethylcyclopropanecarboxylic acid cyano(3-phenoxyphenyl)-methyl ester), permethrin (3-(2,2-dichloroethenyl)-2,2-dimethylcyclopropanecarboxylic acid (3-phenoxyphenyl)-methyl ester) and fenvalerate (4-chloro-alpha-(1-methylethyl)-benzeneacetic acid cyano(3-phenoxyphenyl)methyl ester. Cypermethrin may be prepared as described in DE-A-2326077, permethrin may be prepared as described in DE-A-2437882 and DE-A-2544150, and fenvalerate may be prepared as described in DE-A-2335347. Other pesticides include non-pyrethroid insecticides and acaricides (such as organophosphorus compounds) and herbicides and fungicides. Organophosphorus compounds include chlorpyritos (0,0-diethyl-0-3,5,6-trichloro-2-pyridyl phosphorothioate), chlorpyrifos-methyl (0,0-dimethyl-0-3,5,6-trichloro-2-pyridyl phosphorothioate), fenitrothion (0,0-dimethyl-0-4-nitro-m-tolyl phosphorothioate) and pirimiphos-methyl (0-2-diethylamino-6-methylpyrimidin-4-yl-0,0-dimethyl phosphorothioate).

The present invention is broadly speaking directed to formulating water-insoluble oil-soluble substances in water as small particles whose Z average mean size particle size is less than 200 nm. The Z average mean size can be defined as the model free mean of light scattering. Such formulations include microemulsions, micellar solutions and molecular solutions.

Microemulsions are in themselves known. They are one of three identified types of dispersion (as distinct from a molecular solution) of oil, water and surfactant. (The term "oil" is used in this specification to mean any non-aqueous solvent in which a substance of interest is soluble and which is immiscible with water.) These three types of dispersion are: microemulsions, micellar solutions and normal emulsions (or macroemulsions).

Macroemulsions appear white or opaque and are characterised by their property to separate into their two original liquid phases on standing; the average particle diameter will generally be above 200 nm. Microemulsions and micellar solutions are translucent and do not separate. Microemulsions can be considered as having average droplet (or particle) diameters of from 10 to 200 nm, micellar solutions as having average particle diameters of from 2 nm to 10 nm and molecular solutions as having average particle diameters of less than 2 nm. Recent evidence, however, does suggest that microemulsions with droplet diameters below 10 nm are possible.

Micelles occur when surfactants form large aggregates in water when their concentration is above the critical micelle concentration (cmc); a sharp transition in the physical properties of such solutions occurs at this concentration. In contrast, the physical properties of solutions of surfactants in non-aqueous solvents change gradually as the concentration rises This is due to the fact that the small aggregates are stable in non-aqueous (for example hydrocarbon) solvents, but not in aqueous media, while the opposite is true of relatively large aggregates. Both spherical and cylindrical types of micelles have been recognised. Both of these types involve aggregates of surfactant molecules in which the hydrophobic tails point towards a core, whereas the hydrophilic heads are outwardly directed.

Micellar solutions are observed when water is added to a solution of surfactant in oil or when oil is added to a solution of surfactant in water. The oil and water, which are practically immiscible on their own, can solubilise one another. When oil is solubilised in water, the oil molecules are incorporated between the chains of the surfactant molecules in the micelles: solubilisation can therefore above the cmc. When water is solubilised in oil, it facilitates the aggregation of surfactant molecules as "swollen inverse micelles" in which the polar head groups are embedded in water. Such systems are considered as one phase systems, and the aggregates are spherical or cylindrical.

Turning now to microemulsions, when a cosurfactant such as a medium chain length alcohol is added to a mixture containing oil, water and surfactant, the solubilisate (oil or water) can form a core surrounded by a layer of surfactant and cosurfactant molecules. The globules of oil-in-water or water-in-oil are almost all of the same size, being less than 200 nm (and possibly falling within the range of from 10 to 100 nm).

As with macroemulsions, microemulsions can be of the water-in-oil (w/o) or oil-in-water (o/w) type and can be made to invert from one to another. It is in the area of inversion that microemulsions display peculiar properties. Starting from fluid w/o microemulsions, as water is added, they pass through a viscoelastic gel region and as more water is added they invert to a fluid o/w microemulsion. This process is reversible and the viscoelastic gel region (which can be almost solid) comprises a hexagonal array of water cylinders adjacent to the w/o stage and a lamellar phase of bimolecular leaflets adjacent the o/w stage. These phases of the gel stage are liquid crystalline phases.

Microemulsions have a number of physical properties which can be regarded, either singly or together, as characteristic. One of the properties is the way they scatter light. Microemulsions appear blue to reflected light and orange/red to transmitted light due to the Tyndall effect. Molecules or components of them scatter light. Particles which are large in comparison with the wavelength of light (white light can be taken as having a wavelength of 560 nm for the present purposes) reflect and refract in a regular manner and so appear white. Comparatively small particles scatter light in all directions and to this scattered light is plane polarised. When the droplets of an emulsion are below lambda/4 in diameter, white light can pass through the dispersion and it becomes translucent (or opalescent). Depending upon the relative refractive indices of the components, such systems become transparent (or very translucent).

Rheology may also be used as a characteristic. When dispersed aggregates are other than spherical they offer greater resistance to flow, and this can usually be detected as a sudden and sharp viscosity increase. In the case of microemulsions, the formation of the viscoelastic gel region corresponds to the formation of non-spheroidal aggregates.

Rates of sedimentation can be used to differentiate between macroemulsions and microemulsions. Five minutes in a centrifuge at 100 to $500 \times g$ will normally cause creaming or sedimentation of a macroemulsion. Generally speaking, microemulsions will not separate under such conditions.

Birefringence may also be identified as a characteristic of microemulsions. When very small aggregates are not isotropic, dispersions of them become doubly refracting when they are stirred or allowed to stream. Upon examination between crossed polarised filters, the illuminated field will light up into beautifully coloured patterns. This is due to the scattering and repolarisation of the polarised light.

Conductivity can be used to distinguish between oil continuous microemulsions and oil continuous micellar solutions. For a microemulsion a plot of conductivity against (volume water)/ (volume oil) shows no significant change as water is added until towards the viscoelastic gel region, whereas for micellar solutions as water is added there is a steady increase in conductivity. In both cases the actual plot is somewhat more complex than this simple comparison, which should nevertheless serve as a useful guide. Conductivity may be measured, for example, by a PTI-20 Digital Water Analyzer (Analytical Suppliers, Derby).

One of the best means of differentiating between formulations in accordance with the invention and macroemulsions (and between microemulsions, micellar solutions and molecular solutions) is on the basis of particle or droplet size (usually measured as averages). Average particle or droplet size may be measured with a laser particle sizer, such as the MALVERN AUTOSIZER 2c (Malvern Instruments, Malvern, Hereford & Worcester) using glass cells as sample containers.

Other techniques can be used to determine additional or alternative characteristics of formulations of this invention. These include x-ray studies, electron microscopy, light scattering depolarisation and nmr. In general, nmr measurements are used to resolve theoretical questions regarding the state or location of molecules in microemulsions. The line width for protons in molecules can indicate freedom of the molecules to thermal motion, the broadening of the line indicating greater restriction of motion. The chemical shift of water is different when it is distributed in spheres or in cylindrical or lamellar micelles. Other studies are possible using nmr, in addition.

US-A-4567161 discloses liquid active ingredient concentrates for the preparation of microemulsions. The microemulsions are stated to be oil-in-water microemulsions. The coemulsifiers are a particular class of glycerin esters having HLB (Hydrophilic/Lipophilic Balance) values of between 12 and 18. The formulations of U.S. Pat. No. 4,567,161 are said to have special significance for pharmaceutical active substances. However, the active ingredient can be a number of other substances including herbicides (a number of which are listed), fungicides, insecticides, acaricides, nematocides or plant growth regulators. No specific fungicides, insecticides, acaricides, nematocides or plant growth regulators are disclosed or even suggested.

It has now been found that by choosing coemulsifiers having particular HLB values, it is possible to formulate microemulsions which can invert from w/o formulations to o/w formulations, thereby rendering their use much more flexible. Equally, it is possible to formulate molecular solutions or micellar solutions which form microemulsions on dilution with water. In addition, it has been found that certain formulations of pesticides such as pyrethroids (for example, deltamethrin, cypermethrin or permethrin) show enhanced biological activity.

According to a first aspect of the present invention, there is provided a water-miscible formulation whose average particle size is at most 200 nm, the formulation comprising water, oil, a surfactant and a cosurfactant having an HLB of less than 12.

As indicated above, if the formulation is a microemulsion, the microemulsion will generally be clear or translucent, except in the viscoelastic gel phase. Micellar solutions and molecular solutions may additionally be clear.

The water can be tap water, although distilled water can be used. The amount of water in the microemulsion will depend on many factors but typically for w/o microemulsions will be from 20 to 70% w/v and for o/w microemulsions it shall be from 40 to 95% w/v. Some hardness in the water, although not essential, may in practice be beneficial. Between 100 and 200 ppm hardness (as $CaCO_3$) may be appropriate, particularly around 150 ppm or 160 ppm.

As previously stated, the oil need not merely be an "oil" in the sense of a petroleum fraction, although such oils are included; the term "oil" is used to mean any non-aqueous solvent in which a substance of interest is soluble and which is immiscible with water; alternatively, the substance of interest may itself be the oil. Having said that, the oil may be animal, vegetable, mineral or silicone or some other organic solvent which is water-immiscible, such as an optionally halogenated hydrocarbon. The hydrocarbon may be aliphatic or aromatic or have both aliphatic and aromatic moieties. Typical solvents include xylene, naphthalene, kerosene, isoparaffins and halogenated hydrocarbons.

The surfactant may be any typical emulsifier as found in most macroemulsion systems. The surfactant may be anionic, cationic, zwitterionic or nonionic. Anionic surfactants are more frequently used. Suitable anionic surfactants include hydrocarbon sulphates, sulphonates and sulphamates, especially compounds wherein the hydrocarbon moiety is an alkyl or alkylaryl group. Soaps (hydrocarbyl carboxylates) can also be used, as can sulphocarboxylic acids such as sulphosuccinic acid.

Examples of specific anionic detergents that can be used include alkyl benzene sulphonates and sulphonic acids such as $C_8$ to $C_{16}$ alkyl benzene sulphonates and sulphonic acids including dodecyl benzene sulphonic acid (a predominately straight chain mixture of which compounds is sold under the trade mark NANSA SSA).

The selection of an appropriate surfactant can be made by one of skill in the art without undue experimentation. As a guiding principle, it should be borne in mind that it is highly preferable to match, in a chemical sense, the structure of the surfactant with the structure of the oil. For example, if the oil is aromatic, such as xylene or naphthalene, it is preferred to use a surfactant having an aromatic moiety, for example an alkyl benzene sulphonate or an alkyl naphthalene sulphonate. If the oil is aliphatic, an aliphatic surfactant is preferred such as an alkyl sulphonate or a dialkyl sulphosuccinate (such as dioctyl sulphosuccinate) or a soap. Another factor in determining the choice of surfactant is the type of microemulsion (w/o or o/w) to be produced. Low HLB surfactants (for example having an HLB of from 4 to 9, particularly 4 to 7) tend to stabilise w/o microemulsions and should therefore for preference be used for w/o microemulsions and high HLB surfactants (for example having an HLB of from 9 to 20, particularly 9 to 20) tend to stabilise o/w microemulsions and should thus be used for o/w microemulsions. HLB values may be measured by standard techniques.

After having made the initial selection (eg on the basis of HLB), further selection of the surfactant can be achieved be comparing the hydrophobic portion of the surfactant with the structure of the oil, as discussed above. Polar groups on the surfactant also play an important role and should be considered in the matching process.

An alternative or additional surfactant selection system is based on the phase inversion temperature (PIT) and can therefore be referred to as the PIT system. This system is based upon the temperature at which a surfactant causes an o/w emulsion to invert into a w/o emulsion. It provides information concerning the types of oils, phase volume relationships and the concentration of surfactant which could be used. This system is established on the proposition that the HLB of a nonionic surfactant changes with temperature; the inversion of an emulsion type occurs when the hydrophilic and lipophilic tendencies of the surfactant just balance. No emulsion forms at this temperature. Emulsions stabilised with nonionics tend to be o/w types at low temperatures and w/o types at high temperatures. From the microemulsion standpoint, the PIT system has a useful feature in that it can throw light on the chemical type of surfactant preferred to match a given oil.

Water-miscible formulations in accordance with the first aspect of the invention include a cosurfactant having an HLB of less than 12. Two classes of cosurfactants are normally preferred for use, although others may be used. Aliphatic alcohols (particularly primary aliphatic alcohols) are a first preferred class. They may have a carbon content of from 5 to 12 or more carbon atoms. Lower homologues (for example $C_5$ to $C_7$ alcohols) are used to stabilise certain formulations, including w/o microemulsions and alcohols above $C_8$ (optionally including $C_8$) tend to be used to stabilise other formulations, including o/w microemulsions.

Nonionic surfactants form a more versatile group of cosurfactants. They can be balanced with the primary surfactant to give systems that are stable as micellar solutions and as both w/o and o/w microemulsions. A whole range of nonionics can be used, including ethylene oxide propylene oxide block copolymers (as typified by the PLURONIC PE or PLURIOL PE range from BASF) and alcohol ethoxylates (as typified by the DOBANOL range from Shell).

The HLB of the cosurfactant may be less than 10 or even less than 5. For example, one nonionic cosurfactant is the ethylene oxide propylene oxide block copolymer containing 10% ethylene oxide sold under the trade mark PLURONIC PE 6100 or PLURIOL PE 6100, which has an HLB of 3.0. Other suitable HLB values for cosurfactants are less than 3, for example about 2 or even about 1.

Choosing an appropriate cosurfactant to be formulated with a surfactant and the other components of microemulsions in accordance with the inventions is possible to one of skill in the art without undue experimentation. The methods previously discussed in relation to the choice of surfactant can also be of assistance in the choice of cosurfactant. Further or in the alternative, the technique of cosurfactant partitioning can be of assistance in the preparation of microemulsions. This approach rests on the premise that the condition responsible for the spontaneous formation and stability of microemulsions came about with a zero (or transiently negative) interfacial tension. The total interfacial tension was given by the formula:

$$\gamma_i = \gamma(o/w) - \pi$$

Where
$\gamma_i$ = total interfacial tension
$\gamma(o/w)$ interfacial tension before addition of stabilising agents and
$\pi$ = two dimensional spreading pressure in the monolayer of adsorbed species.

It was then proposed that the initial zero or negative value of the total interfacial tension was the result not so much of a high value of the two dimensional spreading pressure but of the large depression in the value of $(\gamma_{o/w})_a$, so that $\gamma_i = (\gamma_{o/w})_a -$, where $(\gamma_{o/w})_a$ is the interfacial tension after the addition of stabilising agents.

Since most microemulsions appear to form much more readily in the presence of a cosurfactant which is oil soluble, it has been assumed that this material distributed itself between the oil phase and the interface and subsequently changed the composition of the oil so that its interfacial tension was reduced to $(\gamma_{o/w})_a$. This provides a formula with a useful aid to help match emulsifiers (surfactants and cosurfactants) to oils for microemulsification. From an economic standpoint, it is of course desirable only to use a minimum of cosurfactant which is suitable for use in any formulation of the invention under consideration.

Using the cosurfactant partitioning technique, it has been discovered that for any given surfactant, a short chain cosurfactant will tend to produce a w/o system, whereas a long chain cosurfactant will tend to promote an o/w system. In the case of soaps, the larger the size of the (hydrated) cation, the more effective that particular soap will be in promoting an o/w microemulsion.

From the point of view of the present invention, it is immaterial whether the zero interfacial argument as a prerequisite for microemulsion stability is correct. The argument has simply been given as an illustration of how the cosurfactant may be selected. It is accepted that the use of the film balance equation is an over-simplification. From the practical formulator's point of view, however, the expression $(\xi_{5 o/w})_a$ can be valuable.

The relative proportions of the various ingredients of the formulations in accordance with the present invention can vary widely. For w/o microemulsions, micellar solutions and molecular solutions, broad and preferred ranges of the ingredients may be as follows:

| Ingredient | Broad w/v | Preferred w/v |
| --- | --- | --- |
| Oil (including dissolved substance if any) | 20 to 50% | 30 to 40% |
| Surfactant | 1 to 20% | 1 to 5% |
| Cosurfactant | 1 to 20% | 1 to 5% |
| Water | 20 to 70% | 50 to 70% |

In general the amounts of surfactant and cosurfactant should be kept as low as possible and the amount of water should be kept as high as possible. The above is subject always to the proviso that the total number of percentage parts of the ingredients cannot exceed 100.

For o/w microemulsions, the broad and preferred concentration ranges of the ingredients can be as follows:

| Ingredient | Broad w/v | Preferred w/v |
| --- | --- | --- |
| Oil (including dissolved substance if any) | 1 to 20% | 1 to 10% |
| Surfactant | 1 to 10% | 1 to 5% |
| Cosurfactant | 1 to 10% | 1 to 5% |
| Water | 40 to 95% | 70 to 90% |

Again, the above is subject always to the proviso that the total number of percentage parts of the ingredients cannot exceed 100.

A water-insoluble oil-soluble substance which it is desired to formulate may be dissolved in the oil, although it is clear that the oil may itself be the water-insoluble oil soluble substance. This "substance of interest" can be anything which is convenient to be formulated in this manner (including other solvents). As previously stated, pesticides such as synthetic pyrethroids and herbicides are particular candidates for formulation by means of the present invention. Apart from the synthetic pyrethroids, natural pyrethroids, organophosphorus compounds and carbamates are other examples of pesticides useful in the present invention. Mixtures of pesticides (for example mixtures of pyrethroids or mixtures of pyrethroid(s) and organophosphorus compound(s)) may be particularly suitable for some applications. Cypermethrin is an example of a liquid which can function both as the oil and as a water-insoluble oil-soluble substance.

Therefore, according to a second aspect of the present invention, there is provided a water-miscible formulation whose average particle size is at most 200 nm, the formulation including water, oil, a surfactant and a cosurfactant, wherein either the oil is a pesticide or the formulation comprises a pesticide dissolved in the oil. When the oil is a pesticide the formulation may be free of an oily solvent for the pesticide. It is preferred that the cosurfactant has an HLB of less than 12. The pesticide may be a pyrethroid or any other insecticide, acaricide, herbicide or fungicide. Other preferred features of this second aspect of the invention are as for the first aspect mutatis mutandis.

With water-in-oil microemulsions, micellar solutions and molecular solutions, it is generally possible to get a higher concentration of the substance of interest (for example deltamethrin or another synthetic pyrethroid or other pesticide). However, o/w formulations may give a perfectly adequate concentration for end use or even for concentrates for dilution before use.

In principle, formulations in accordance with the invention can be made very simply. Therefore, according to a third aspect of the present invention, a formulation in accordance with the first or second aspect is prepared by mixing the ingredients. Depending on the thermodynamic favourability of the system, the ingredients will tend to form a microemulsion, micellar solution or molecular solution. In practice, however, kinetic considerations may dictate that some agitation is preferably used to assist the mixing. Agitation may be by magnetic or mechanical means or in some cases ultrasonic.

Once a desired and correctly balanced formulation has been arrived at, it will be found that the order of addition of the ingredients is not normally critical. However, for w/o microemulsions, micellar solutions and molecular solutions, it is preferred to add the ingredients to a vessel in the following order:
1. Add the oil to a vessel
2. Add any additives such as solid deltamethrin dissolved in further oil
3. Add the surfactant and cosurfactant and dissolve them in the oil
4. Add water to give a clear formulation (eg a w/o microemulsion)

Although the above procedure may be found to be suitable for o/w microemulsions, there is a possibility that upon addition of the water, the system could move into the viscoelastic gel region (which can be almost solid) and this could cause practical mixing problems. Consequently, the following procedure is preferred for the preparation of o/w microemulsions:
1. The oil is added to the vessel
2. Additives (such as solid deltamethrin) is dissolved in the oil
3. The surfactant is added and dissolved in the oil
4. Water is added and agitated to give a homogeneous macroemulsion
5. The cosurfactant is added and the system is agitated to produce a clear o/w microemulsion.

Routine modifications, such as the application of heat or altering the degree of agitation can be made to these basic processes to suit the system in use.

It has been stated above that the preferred pyrethroid or other pesticidal microemulsion formulations have been found to have enhanced pesticidal activity Therefore, according to a fourth aspect of the present invention there is provided a method of controlling pests, the method comprising applying a pesticide in a formulation whose average particle size is at most 200 nm. The formulation may be a microemulsion, a micellar solution or a molecular solution; the microemulsion may be an o/w or a w/o formulation. Oil-in-water microemulsion formulations are preferred. The formulation will generally comprise water, a pesticidal oil, a surfactant and a cosurfactant, preferably having an HLB of less than 12. Pyrethroid or other pesticides formulated in this way can be used to control pests in an agricultural environment, for example on a field of crops. Examples of crops include grain, brassica such as cabbages and fruit such as apples and pears. The pests may be insects or acarines or may be aphids; the pests may be in larval form. Another application is in bulk grain storage, where the bulk grain is suceptible to a variety of pests. In particular, in warm climates such as the southern United States and Australia the lesser grain borer weevil (*Rhyzopertha dominica*) has caused considerable economic loss and has proved difficult to control using conventional formulations. Formulations in accordance with the invention have been found to be surprisingly efficacious in dealing with such pests. In particular, formulations of the invention have high activity, surprising persistence and can allow for precisely controlled even dosing of the pesticise over the material to be protected. Treatment against borer pests in general may be achieved by means of the present invention.

Applications of such pyrethroid or other (for example, organophosphorus) pesticide formulations are not confined to agriculture: public health formulations may be commercially important. Agricultural formulations in accordance with the invention may have a further advantage in that they use less potentially harmful solvent (such as xylene) per dose than certain conventional formulations, thereby posing less of a threat to the crop being treated, the handler and to the environment in general.

According to a fifth aspect of the invention, there is provided a method for controlling pests in stored grain, the method comprising applying to a locus for the pests (for example stored grain, or a container for stored grain) a water-miscible formulation whose average particle size is at most 200 nm, the formulation including water, oil, a surfactant, a cosurfactant, wherein either the oil is a pesticide or the formulation comprises a pesticide dissolved in the oil.

Other preferred features of the fourth and fifth aspects are as for the first aspect *mutatis mutandis*.

The concentration of the substance of interest (for example, deltamethrin) in the formulations of the invention may range from as little as 0.1 ppm, 0.01 g/l or 0.1 g/l up to 100 or 200 g/l or more. High concentrations of pesticide may range from 10 to 300 g/l, for example 25 to 200 g/l, such as 25 or 100 g/l. For agricultural use of deltamethrin or another pyrethroid pesticide 10 to 50 g/l or 100 g/l final concentration may be found to be suitable. For public health or stored grain use, a formulation containing from 0.1 ppm or 0.05 g/l to 5 g/l, for example 0.1 g/l to 1 g/l may be found to be acceptable. The invention will be illustrated by the following examples.

EXAMPLE 1

A w/o microemulsion was made up from the following ingredients:

| | |
|---|---|
| xylene/deltamethrin concentrate[1] | 200 ml/l |
| xylene | 200 ml/l |
| PLURIOL PE 6100[2] | 150 g/l |
| NANSA SSA[3] | 130 g/l |
| Water (tap) | 345 g/l |

Notes:
[1] The concentrate contained 125 g/l deltamethrin and gives a final concentration of 25 g/l
[2] Trade mark for ethylene oxide propylene oxide block copolymer containing 10% ethylene oxide, HLB 3.0 - nonionic surfactant functioning as cosurfactant.
[3] Trade mark for dodecyl benzene sulphonic acid - predominantly straight chain (anionic surfactant).

A liter of the above formulation was prepared by first adding 200 ml xylene to a beaker. 200 ml of the xylene/deltamethrin concentrate was then added to the same beaker. The surfactant and cosurfactant were then added and dissolved in the oil phase. The water was then added, with stirring, to give a clear w/o microemulsion. The formulation was confirmed to be a microemulsion by conductivity measurements. The average particle size of a 1/400 dilution was measured by a MALVERN AUTOSIZER 2c laser particle sizer to be 62.8±11.8 nm.

EXAMPLE 2

A formulation was prepared from the following ingredients:

| | |
|---|---|
| Deltamethrin | 0.4 g/l |
| Xylene | 25.75 g/l |
| NANSA SSA[2] | 36 g/l |
| Propylene oxide/ethylene oxide copolymer* | 41.2 g/l |
| Water | 906 g/l |

*Cosurfactant: Molar mass of polypropylene oxide portion = 1750 g/mol; percentage of polyethylene oxide in total molecule = 10%.

A liter of the above formation was prepared by first adding the xylene to a beaker. Solid deltamethrin was then added and dissolved in the xylene. The NANSA SSA surfactant was then added and dissolved in the oily phase. Subsequently, water was added and the mixture agitated to give a homogeneous macroemulsion. Finally, the (PLURIOL PE 6100) cosurfactant was added and the entire system agitated to produce a clear formulation. The average particle size was measured by a MALVERN AUTOSIZER 2c laser particle sizer to be 0.8 nm, which indicates that the formulation is a molecular solution.

EXAMPLE 3

A formulation was prepared from the following ingredients:

| | |
|---|---|
| Xylene/cypermethrin[1] | 400 ml/l |
| PLURIOL PE 6100 | 150 g/l |
| NANSA SSA | 130 g/l |
| Water | 345 g/l |

Note:
[1] 100 g cypermethrin (technical) made up to 400 ml with xylene.
(2) Trade mark for dodecyl benzene sulphonic acid - predominantly straight chain (anionic surfactant).

20 g cypermethrin were made up to 80 ml with xylene, and the resulting mixture was placed in a 250 ml beaker. The PLURIOL PE 6100 surfactant and NANSA SSA cosurfactant were then slowly dissolved into this and the appropriate amount of water (69.0 mls) added slowly from a burette while stirring. The formulation was confirmed to be a micellar solution by conductivity measurements. The average particle size of a 1/400 dilution was measured by a MALVERN AUTOSIZER 2c laser particle sizer to be 40.2±6.9 nm, showing the diluted formulation to be a microemulsion.

EXAMPLE 4

A ready-for-use formulation was made up from the following ingredients:

| | |
|---|---|
| K'OTHRINE 50[1] | 8.0 ml/l |
| Xylene | 2.0 ml/l |
| PLURONIC PE 10 100[2] | 9.0 g/l |
| NANSA SSA | 6.0 g/l |

-continued

| | |
|---|---|
| Water | 976.0 g/l |

Notes:
(1) A 50 g/l solution of deltamethrin in xylene
(2) Trade mark for ethylene oxide propylene oxide block copolymer containing 10% ethylene oxide, HLB 3.0 - nonionic surfactant functioning as cosurfactant.

The K'OTHRINE and xylene were mixed and the surfactants dissolved into them; then the water was added from a burette with constant stirring. The average particle size was measured by a MALVERN AUTOSIZER 2c laser particle sizer to be 15.0±2.2 nm, showing the formulation to be on the lower size limit for a microemulsion.

EXAMPLE 5

A ready-for-use formulation was made up from the following ingredients:

| | |
|---|---|
| K'OTHRINE 50(1) | 8.0 ml/l |
| Xylene | 2.0 ml/l |
| PLURONIC PE 10 100(2) | 12.0 g/l |
| NANSA SSA | 8.0 g/l |
| Water | 917.0 g/l |

Notes:
(1) A 50 g/l solution of deltamethrin in xylene
(2) Trade mark for ethylene oxide propylene oxide block copolymer containing 10% ethylene oxide, HLB 3.0 - nonionic surfactant functioning as cosurfactant.

The K'OTHRINE and xylene were placed in a beaker. To this the PLURIOL and NANSA were added; then this was well mixed. The water was added to this mixture with constant stirring. The average particle size was measured by a MALVERN AUTOSIZER 2c laser particle sizer to be 4.1±1.4 nm, showing the formulation to be a micellar solution.

EXAMPLE 6

A formulation was made up from the following ingredients:

| | |
|---|---|
| K'OTHRINE 50(1) | 40.0 ml/l |
| NANSA SSA | 34.2 g/l |
| PLURONIC PE 6200(2) | 41.8 g/l |
| Filtered Tap Water | 889 g/l |

Notes:
(1) A 50 g/l solution of deltamethrin in xylene
(2) Trade mark for ethylene oxide propylene oxide block copolymer containing 20% ethylene oxide - nonionic surfactant functioning as cosurfactant.

40 ml K'OTHRINE, 34.2 g NANSA SSA and 41.8 g PLURIOL PE 6200 were placed in a beaker and then mixed with a stirrer. Then the 889 g water was added to this mixture with constant stirring. The average particle size was measured by MALVERN AUTOSIZER 2c laser particle sizer to be 0.8 nm, showing the formulation to be a molecular solution. An 8% dilution had an average particle size of 73.0±14.3 nm, measured similarly, showing the diluted formulation to be a microemulsion.

EXAMPLE 7

A formulation was made up from the following ingredients:

| | |
|---|---|
| Cypermethrin | 50 g/l |
| Xylene | 38.5 g/l |
| PLURIOL PE 8100(1) | 100 g/l |
| NANSA SSA | 53.8 g/l |
| Water | 757.7 g/l |

Note:
(1) Trade mark for ethylene oxide propylene oxide block copolymer containing 10% ethylene oxide (HLB = 2) - nonionic surfactant functioning as cosurfactant.

The cypermethrin was dissolved in the xylene; to this the PLURIOL PE 8100 and NANSA SSA were added and mixed in well. The water was added slowly with constant stirring until clear. The average particle size of a 1/400 dilution in water was measured by a MALVERN AUTOSIZER 2c laser particle sizer to be 41.2±7.0 nm, showing the formulation to be a microemulsion.

EXAMPLE 8

A formulation was made up from the following ingredients:

| | |
|---|---|
| Cypermethrin | 50 g/l |
| PLURIOL PE 8100(1) | 130 g/l |
| NANSA SSA | 70 g/l |
| Water | 750 g/l |

Note:
(1) Trade mark for ethylene oxide propylene oxide block copolymer containing 10% ethylene oxide (HLB = 2) - nonionic surfactant functioning as cosurfactant.

The cypermethrin was dissolved in the PLURIOL PE 8100 and NANSA SSA. The water was added slowly with constant stirring until clear. The average particle size was measured by a MALVERN AUTOSIZER 2c laser particle sizer to be 7.8±1.6 nm, showing the formulation to be a micellar solution. It is expected that a microemulsion would be formed on dilution.

EXAMPLE 9

A formulation was made up from the following ingredients:

| | |
|---|---|
| Cypermethrin | 95.6 g/l |
| Xylene | 36.8 g/l |
| PLURIOL PE 8100(1) | 124.3 g/l |
| NANSA SSA | 66.9 g/l |
| Water | 676.4 g/l |

Note:
(1) Trade mark for ethylene oxide propylene oxide block copolymer containing 10% ethylene oxide (HLB = 2) - nonionic surfactant functioning as cosurfactant.

The cypermethrin was dissolved in the xylene. To this the PLURIOL PE 8100 and NANSA SSA were added and mixed in well. The water was added slowly with constant stirring until clear. The average particle size was measured by a MALVERN AUTOSIZER 2c laser particle sizer to be 40.6±7.4 nm, showing the formulation to be a microemulsion.

EXAMPLE 10

A formulation was made up from the following ingredients:

| | |
|---|---|
| Cypermethrin | 100 g/l |
| PLURIOL PE 8100(1) | 154 g/l |
| NANSA SSA | 83 g/l |
| Water | 663 g/l |

Note:
(1) Trade mark for ethylene oxide propylene oxide block copolymer containing 10% ethylene oxide (HLB = 2) - nonionic surfactant functioning as cosurfactant.

The cypermethrin was dissolved in the PLURIOL PE 8100 and NANSA SSA. The water was added slowly with constant stirring until clear. The average particle size was measured by a MALVERN AUTOSIZER 2c laser particle sizer to be 18.1±3.9 nm, showing the formulation to be a microemulsion.

EXAMPLE 11

Following the general procedure of Example 1, a microemulsion of fenvalerate was prepared to a final concentration of 100 g/l.

EXAMPLE 12

A formulation was made up from the following ingredients:

| Fenitrothion | 175 g/l |
|---|---|
| Deltamethrin | 25 g/l |
| Xylene | 180 g/l |
| PLURIOL PE 8100 | 150 g/l |
| NANSA SSA | 100 g/l |
| Water | 400 g/l |

The fenitrothion and the deltamethrin were dissolved in the xylene; to the resulting solution the PLURIOL PE 8100 and the NANSA SSA were added with stirring. Then the water was added slowly with constant stirring until clear. The average particle size of a 1/400 dilution in water was measured by a MALVERN AUTOSIZER 2c laser particle sizer to be 41.5±11.4 nm, showing the diluted formulation to be a microemulsion.

EXAMPLE 13

A formulation was made up from the following ingredients:

| Chlorpyrifos-methyl | 175 g/l |
|---|---|
| Deltamethrin | 25 g/l |
| Xylene | 180 g/l |
| PLURIOL PE 8100 | 150 g/l |
| NANSA SSA | 100 g/l |
| Water | 400 g/l |

The chlorpyrifos-methyl and the deltamethrin were dissolved in the xylene; to the resulting solution the PLURIOL PE 8100 and the NANSA SSA were added with stirring. Then the water was added slowly with constant stirring until clear. The average particle size of a 1/400 dilution in water may be measured by a MALVERN AUTOSIZER 2c laser particle sizer to be about 40 nm, showing the diluted formulation to be a microemulsion.

EXAMPLE 14

A formulation was made up from the following ingredients:

| Fenitrothion | 150 g/l |
|---|---|
| Cypermethrin | 50 g/l |
| Xylene | 180 g/l |
| PLURIOL PE 8100 | 150 g/l |
| NANSA SSA | 100 g/l |
| Water | 400 g/l |

The fenitrothion and the cypermethrin were dissolved in the xylene; to the resulting solution the PLURIOL PE 8100 and the NANSA SSA were added with stirring. Then the water was added slowly with constant stirring until clear. The average particle size of a 1/400 dilution in water may be measured by a MALVERN AUTOSIZER 2c laser particle sizer to be about 40 nm, showing the diluted formulation to be a microemulsion.

EXAMPLE 15

A formulation was made up from the following ingredients:

| Chlorpyrifos-methyl | 150 g/l |
|---|---|
| Cypermethrin | 50 g/l |
| Xylene | 180 g/l |
| PLURIOL PE 8100 | 150 g/l |
| NANSA SSA | 100 g/l |
| Water | 400 g/l |

The chlorpyrifos-methyl and the cypermethrin were dissolved in the xylene; to the resulting solution the PLURIOL PE 8100 and the NANSA SSA were added with stirring. Then the water was added slowly with constant stirring until clear. The average particle size of a 1/400 dilution in water may be measured by a MALVERN. AUTOSIZER 2c laser particle sizer to be about 40 nm, showing the diluted formulation to be a microemulsion.

EXAMPLE A

A deltamethrin microemulsion as prepared in Example 1 was used to treat a crop of cabbages in south Nottinghamshire, most of the plants of which were infested with 2 to 4 small colonies of grey aphids, with some caterpillars being present. The weather conditions were sunny and the temperature was 16°. The formulation of Example 1 was applied at rates of 50, 70, 150 and 450 mls/ha and compared with a control (DECIS deltamethrin) formulation of comparable concentration. The DECIS formulation was applied at rates of 50, 75 and 150 mls/ha. These treatments, together with the untreated control are set out in Table 1. The word DECIS is a trade mark.

TABLE 1

| Treatment No. | Product | Rate mls/ha |
|---|---|---|
| 1 | Untreated | — |
| 2 | Example 1 | 50 |
| 3 | Example 1 | 75 |
| 4 | Example 1 | 150 |
| 5 | Example 1 | 450 |
| 6 | DECIS | 50 |
| 7 | DECIS | 75 |
| 8 | DECIS | 150 |

N rate was chosen as 150 mls/ha i.e. the maintenance rate normally used in a repeat application programme. This rate was chosen to challenge the products at below normal full efficacy rates.

The results were assessed by treating the number of live aphid colonies per plant after treatment. The experiment comprised four replicates, each of which consisted of examining 25 plants. In other words, 100 plants were assessed per treatment. The number of colonies remaining, as well as the degree (percent) control of pests, compared to the untreated plants, are shown in Table 2.

TABLE 2

| Treatment No | 1 | 2 | 3 | 4 | 5 | 6 | 7 | 8 |
|---|---|---|---|---|---|---|---|---|
| Rate (mls/ha) | 0 | 50 | 75 | 150 | 450 | 50 | 75 | 150 |
| Rep 1 | 47.0 | 10.0 | 6.0 | 6.0 | 4.0 | 28.0 | 19.0 | 11.0 |
| Rep 2 | 33.0 | 14.0 | 13.0 | 7.0 | 0 | 28.0 | 17.0 | 14.0 |
| Rep 3 | 34.0 | 17.0 | 8.0 | 5.0 | 3.0 | 20.0 | 13.0 | 7.0 |
| Rep 4 | 38.0 | 12.0 | 11.0 | 7.0 | 6.0 | 15.0 | 12.0 | 12.0 |
| Total | 152.0 | 53.0 | 38.0 | 25.0 | 13.0 | 91.0 | 61.0 | 44.0 |
| Mean | 38.0 | 13.3 | 9.5 | 6.3 | 3.3 | 22.8 | 15.3 | 11.0 |
| % Control of untreated | | 65.1 | 75.0 | 83.6 | 91.4 | 40.1 | 59.9 | 71.1 |

Least significant difference between means:
4.14 at 95% probability
5.65 at 99% probability
7.60 at 99.9% probability The results may be analysed as follows:

TABLE 3

| Rate (mls/ha) | % control | | Example 1/DECIS (%) | % improvement |
|---|---|---|---|---|
| | Example 1 | DECIS | | |
| 50 | 65.1 | 40.1 | 162 | 62 |
| 75 | 75.0 | 59.9 | 125 | 25 |
| 150 | 83.6 | 71.1 | 117 | 17 |

From Table 3, and from FIG. 1 which graphically shows the percentage control as a function of the application rate for the formulation of Example 1 and the Decis formulation, it can be seen that microemulsions in accordance with the present invention are more active than conventional non-microemulsion formulations. The microemulsion of Example 1 shows improvements of between 15 and 60% over the standard formulation, depending upon the rates used; and it appears to reach commercial acceptability, that is to say more than 70% control at about 60 mls/ha.

EXAMPLE B

The approximate $LD_{50}$ of the microemulsions of Examples 1, 3 and 11 against blowfly larvae were determined by topical application of 1 microliter at various dilutions and compared with corresponding $LD_{50}$s of corresponding emulsifiable concentrates (ECs). The results are shown in Table 4:

TABLE 4

| Active inged't | Approximate $LD_{50}$ | (mcg/insect) | Ratio |
|---|---|---|---|
| & concn | Microemulsion | Standard EC | M:EC |
| Deltamethrin (25 g/l) | 0.076 | 0.145 | 0.52 |
| Cypermethrin (100 g/l) | 0.100 | 0.200 | 0.5 |
| Fenvalerate | 0.342 | 0.617 | 0.55 |

For the three pyrethroids tested. It can be seen that there is the same order of reduction in the $LD_{50}$ value, that is to say about 50%.

EXAMPLE C

A cypermethrin formulation as prepared in Example 3 was used to treat a crop of Discovery apples in south Nottinghamshire which were infested with tortrix larvae. The formulation of Example 3 was diluted at rates of 2.5, 3.3, 5.0 and 10.0 ml/20 l and compared with a control (AMBUSH C cypermethrin) formulation. The AMBUSH C formulation was diluted at rates of 2.5, 5.0 and 10 ml/20 l. (10.0 ml AMBUSH C per 20 liters is the normal dilution rate for this product.) These treatments, together with the untreated control are set out in Table 5. The word AMBUSH is a trade mark.

TABLE 5

| Treatment No. | Product | Rate ml/20 l |
|---|---|---|
| 1 | Untreated | — |
| 2 | Example 3 | 2.5 |
| 3 | Example 3 | 3.3 |
| 4 | Example 3 | 5.0 |
| 5 | Example 3 | 10.0 |
| 6 | AMBUSH C | 2.5 |
| 7 | AMBUSH C | 5.0 |
| 8 | AMBUSH C | 10.0 |

The results were assessed by measuring the number of live larvae three days after treatment; weak or dead larvae had been removed by a heavy storm prior to assessment. The experiment comprised four replicates. The number of larvae remaining, as well as the degree (percent) control of larvae compared to the untreated plants, are shown in Table 6.

TABLE 6

| Treatment No | 1 | 2 | 3 | 4 | 5 | 6 | 7 | 8 |
|---|---|---|---|---|---|---|---|---|
| Rate (ml/20 l) | 0 | 2.5 | 3.3 | 5.0 | 10.0 | 2.5 | 5.0 | 10.0 |
| Rep 1 | 5 | 0 | 0 | 0 | 1 | 1 | 0 | 0 |
| Rep 2 | 3 | 0 | 0 | 0 | 0 | 0 | 1 | 0 |
| Rep 3 | 4 | 0 | 0 | 0 | 0 | 1 | 0 | 0 |
| Rep 4 | 3 | 0 | 0 | 0 | 0 | 1 | 0 | 0 |
| Total | 15 | 0 | 0 | 0 | 1 | 3 | 1 | 0 |
| % Control of untreated | | 100.0 | 100.0 | 100.0 | 93.4 | 80.0 | 93.4 | 100.0 |

From Table 6 it can be seen that a formulation in accordance with the invention is as effective, even at lower active ingredient concentrations, than a conventional formulation.

EXAMPLE D

The formulation of Example 3 was tested against various insect and mite pests (namely *Oryzaephilus surinamensis, Sitophilus granarius, Tribolium castaneum* (insects) and *Acarus siro* and *Glycyphagus destructo* (mites)) and compared with a standard preparation of pirimiphos-methyl, supplied as a 25% w/v emulsifiable concentrate. At active ingredient rates of 1 ppm and 2 ppm the performance of the Example 3 formulation was similar to the performance of the standard preparation; but at active ingredient rates of 0.5 ppm and 0.25 ppm the formulation of Example 3 outperformed the standard preparation.

EXAMPLE E

The formulation of Example 3 was tested against the lesser grain borer weevil (*Rhyzopertha dominica*) and compared with a standard preparation of pirimiphos-methyl, supplied as a 25% w/v emulsifiable concentrate. The formulation of Example 3 at an active ingredient rate of 0.15ppm gave comparable performance to the standard preparation at an active ingredient rate of 0.25 ppm.

EXAMPLE F

The formulation of Example 3 was tested against the lesser grain borer weevil (*Rhyzopertha dominica*) in a six month study. The knockdown count was measured at the following intervals after the start of the study and at the following concentrations:

| Knockdown (%) | Week 1 | Month 2 | Month 4 | Month 6 |
|---|---|---|---|---|
| 0.125 mg/kg | 97 | 92 | 92 | 68 |
| 0.25 mg/kg | 100 | 99 | 100 | 98 |
| 0.5 mg/kg | 100 | 100 | 100 | 100 |
| 1.0 mg/kg | 100 | 100 | 100 | 100 |
| 2.0 mg/kg | 100 | 100 | 100 | 100 |

The results are illustrated graphically in FIG. 1. It can be seen that the initial high level of activity is substantially maintained throughout the length of the study.

COMPARATIVE EXAMPLE G

A commercially available macroemulsified formulation of cypermethrin was tested under identical conditions to Example F against the lesser grain borer weevil (*Rhyzopertha dominica*) in a six month study. The knockdown count was measured at the following intervals after the start of the study and at the following concentrations:

| Knockdown (%) | Week 1 | Month 2 | Month 4 | Month 6 |
|---|---|---|---|---|
| 0.125 mg/kg | 100 | 0 | 0 | 0 |
| 0.25 mg/kg | 100 | 0 | 0 | 0 |
| 0.5 mg/kg | 100 | 0 | 0 | 0 |
| 1.0 mg/kg | 100 | 0 | 0 | 0 |
| 2.0 mg/kg | 100 | 0 | 0 | 0 |

Figure 2:
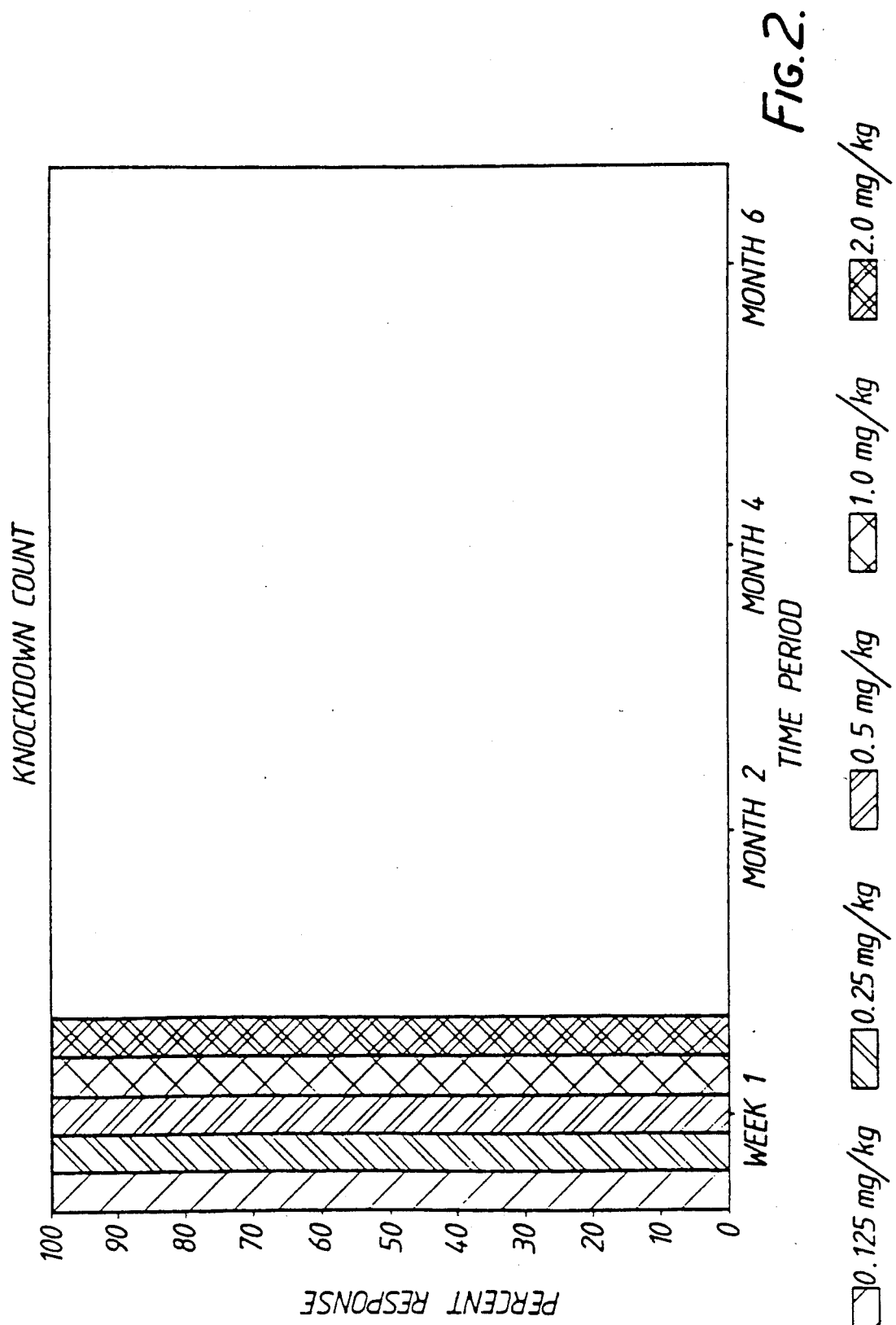

The results are illustrated graphically in FIG. 2. It can be seen that the initial high level of activity is not maintained throughout the length of the study, in contrast to the formulations of the invention.

COMPARATIVE EXAMPLE H

A commercially available macroemulsified formulation of pirimiphos-methyl was tested under identical conditions to Example F against the lesser grain borer weevil (*Rhyzopertha dominica*) in a six month study. The knockdown count was measured at the following intervals after the start of the study and at the following concentrations:

| Knockdown (%) | Week 1 | Month 2 | Month 4 | Month 6 |
|---|---|---|---|---|
| 0.125 mg/kg | 8 | 2 | 2 | 0 |
| 0.25 mg/kg | 69 | 1 | 1 | 4 |
| 0.5 mg/kg | 98 | 4 | 5 | 5 |
| 1.0 mg/kg | 99 | 2 | 10 | 8 |
| 2.0 mg/kg | 98 | 8 | 16 | 7 |

Figure 3:
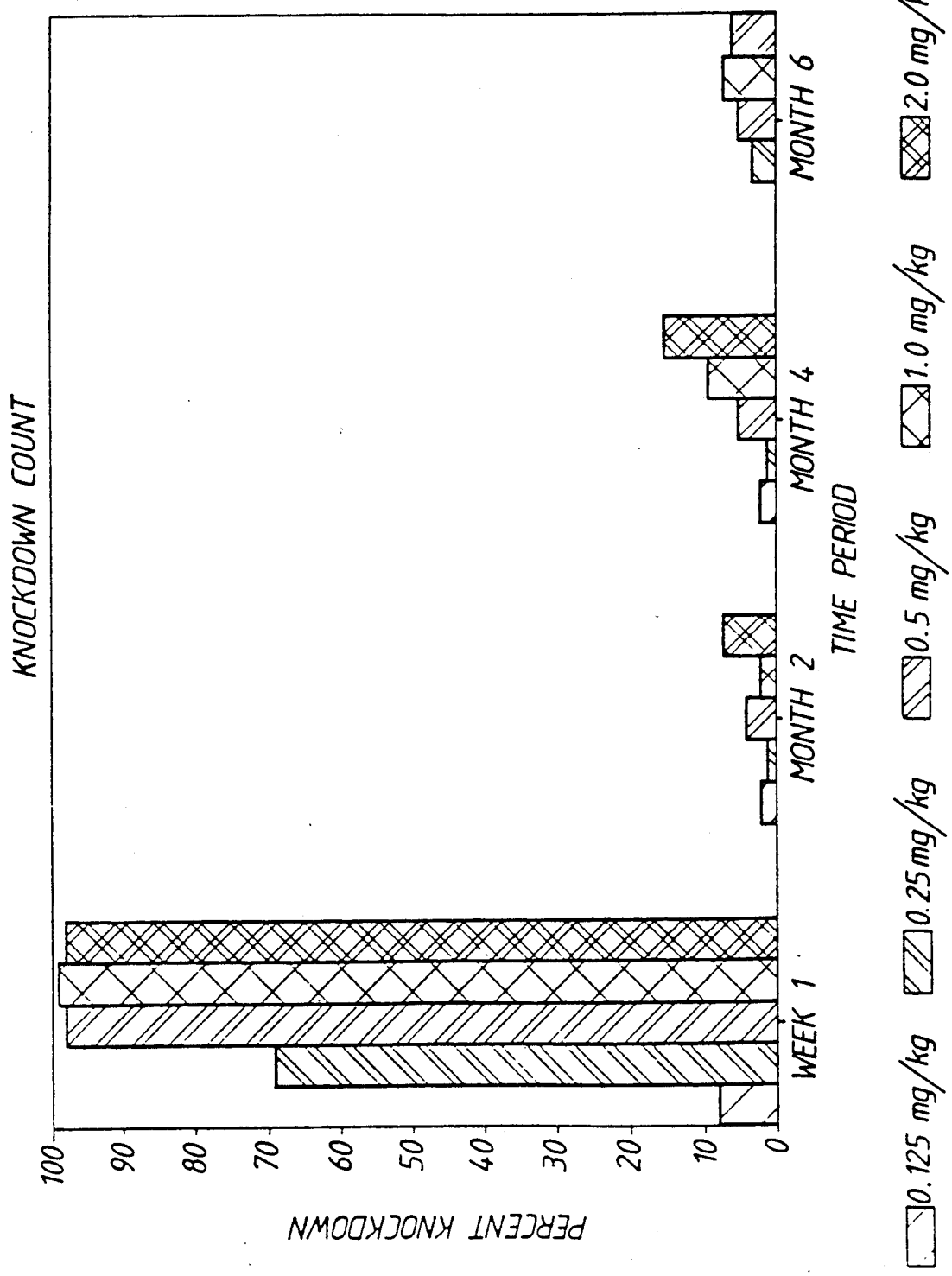

The results are illustrated graphically in FIG. 3. It can be seen that the initial high level of activity is maintained only to a small degree throughout the length of the study, in contrast to the formulations of the invention.

I claim:

1. A water-miscible formulation which is a microemulsion, a micellar solution or a molecular solution and whose average particle size is at most 200 nm, the formulation including water, a water-insoluble, oil-soluble pesticidal oil, a surfactant and a cosurfactant, wherein either the pesticidal oil is a pesticide or the pesticidal oil comprises a pesticide dissolved in oil, the cosurfactant comprising a nonionic surfactant having a hydrophile-lipophile balance (HLB) of less than 10.

2. A formulation as claimed in claim 1, wherein the cosurfactant comprises an ethylene oxide propylene oxide block copolymer or an alcohol ethoxylate.

3. A formulation as claimed in claim 2, wherein the cosurfactant comprises an ethylene oxide propylene oxide block copolymer.

4. A formulation as claimed in claim 1, wherein the surfactant is an anionic surfactant.

5. A formulation as claimed in claim 4, wherein the surfactant is a hydrocarbon sulphonic acid.

6. A formulation as claimed in claim 5, wherein the hydrocarbon sulphonic acid is an alkyl or alkylaryl sulphonic acid.

7. A formulation as claimed in claim 5, wherein the hydrocarbon sulphonic acid is a $C_8$–$C_{16}$ alkyl benzene sulphonate.

8. A formulation as claimed in claim 1, 2 or 3, wherein the pesticidal oil consists substantially only of a pesticide.

9. A formulation as claimed in claim 1, 2 or 3, wherein the formulation comprises on a w/v basis: oil (20 to 50%), surfactant (1 to 20%), cosurfactant (1 to 20%) and water (20 to 70%), provided that the total number of percentage parts of the ingredients cannot exceed 100.

10. A formulation as claimed in claim 1, 2 or 3, wherein the formulation comprises on a w/v basis: oil (1 to 20%), surfactant (1 to 10%), cosurfactant (1 to 10%) and water (40 to 95%), provided that the total number of percentage parts of the ingredients cannot exceed 100.

11. A method of protecting stored grain against pests, the method comprising applying to grain a pesticidal formulation which is a microemulsion, a micellar solution or a molecular solution and whose average particle size is at most 200 nm, the formulation including water, oil, a surfactant and a cosurfactant, wherein either the oil is a pesticide or the formulation comprises a water-insoluble, oil-soluble pesticide dissolved in the oil.

12. A method as claimed in claim 11, wherein the formulation is as claimed in any one of claims 1, 2 or 3.

13. A water-miscible formulation which is a microemulsion, a micellar solution or a molecular solution and whose average particle size is at most 200 nm, the formulation comprising water, oil, a surfactant and a cosurfactant having an HLB of less than 10.

14. A formulation as claimed in claim 1, wherein the pesticide is a pyrethroid.

15. A formulation as claimed in claim 1, 2 or 3, wherein the formulation is a microemulsion.

16. A method as claimed in claim 11, wherein the formulation is a microemulsion.

17. A method as claimed in claim 11, wherein the cosurfactant comprises a nonionic surfactant.

18. A method as claimed in claim 17, wherein the nonionic surfactant has a hydrophile-lipophile balance of less than 12.

19. A method as claimed in claim 11, wherein the cosurfactant is oil-soluble.

* * * * *

UNITED STATES PATENT AND TRADEMARK OFFICE
CERTIFICATE OF CORRECTION

PATENT NO. : 5,037,653
DATED : August 6, 1991
INVENTOR(S) : DAWSON

It is certified that error appears in the above-indentified patent and that said Letters Patent is hereby corrected as shown below:

On the Title Page:
Item 86, wherein "Nov. 20, 1988" (both occurrences) should read --Nov. 20, 1989--.

Column 6, line 42, (first occurrence) delete "$\gamma$; = (65 (o/w)a) -, and insert -- $\gamma$; = ($\eta$(o/w)a) - $\pi$ --; (second occurrence) delete "(65 (0/w)a)" and insert --( $\eta$ (o/w)a)--.

Signed and Sealed this

Twelfth Day of July, 1994

Attest:

BRUCE LEHMAN

Attesting Officer          Commissioner of Patents and Trademarks